United States Patent [19]

Kopetzki et al.

[11] Patent Number: 5,672,691
[45] Date of Patent: Sep. 30, 1997

[54] RECOMBINANT CORE STREPTAVIDIN

[75] Inventors: Erhard Kopetzki, Penzberg; Rainer Rudolph, Weilheim; Adelbert Grossmann, Eglfing, all of Germany

[73] Assignee: Boehringer Mannheim GmbH, Mannheim, Germany

[21] Appl. No.: 434,718

[22] Filed: May 4, 1995

Related U.S. Application Data

[62] Division of Ser. No. 211,833, Apr. 28, 1994, Pat. No. 5,489,528.

[30] Foreign Application Priority Data

Oct. 28, 1991 [DE] Germany .......................... 41 35 543.1

[51] Int. Cl.$^6$ .............................. C07K 1/22; C07K 14/36; G01N 33/53
[52] U.S. Cl. ........................... 530/413; 530/350; 436/501
[58] Field of Search ................................. 530/350, 413

[56] References Cited

U.S. PATENT DOCUMENTS 5,328,985  7/1994  Sano et al. ............................. 530/350

OTHER PUBLICATIONS

Sambrook et al., Molecular Cloning: A Laboratory Manual, Second Edition, Cold Spring Harbor Lab. Press, Cold Spring Harbor, NY, pp. 17.10–17.21 1989.

Bayer et al., Biochem J. 259:369–376 (1989).

Sano et al., Biochem. Biophys. Res. Comm. 176:571–577 (1991).

Sano et al., Proc. Natl. Acad. Sci. USA 87:142–146 (1990).

Bayer et al., Meth. Enzymol. 184:80–89 (1990).

*Primary Examiner*—Robert A. Wax
*Assistant Examiner*—Eric Grimes
*Attorney, Agent, or Firm*—Nikaido, Marmelstein, Murray & Oram LLP

[57] ABSTRACT

The present invention concerns a process for the isolation of recombinant core streptavidin in which host cells are transformed with a DNA coding for core streptavidin, the transformed host cells are cultured under suitable conditions, the DNA coding for core streptavidin is expressed and the recombinant core streptavidin is isolated from the host cells or the culture medium, wherein a DNA coding for core streptavidin is used which has (a) the nucleotide sequence shown in SEQ ID NO. 1 or
(b) a nucleotide sequence corresponding to the nucleotide sequence (a) within the scope of the degeneracy of the genetic code.

2 Claims, 3 Drawing Sheets

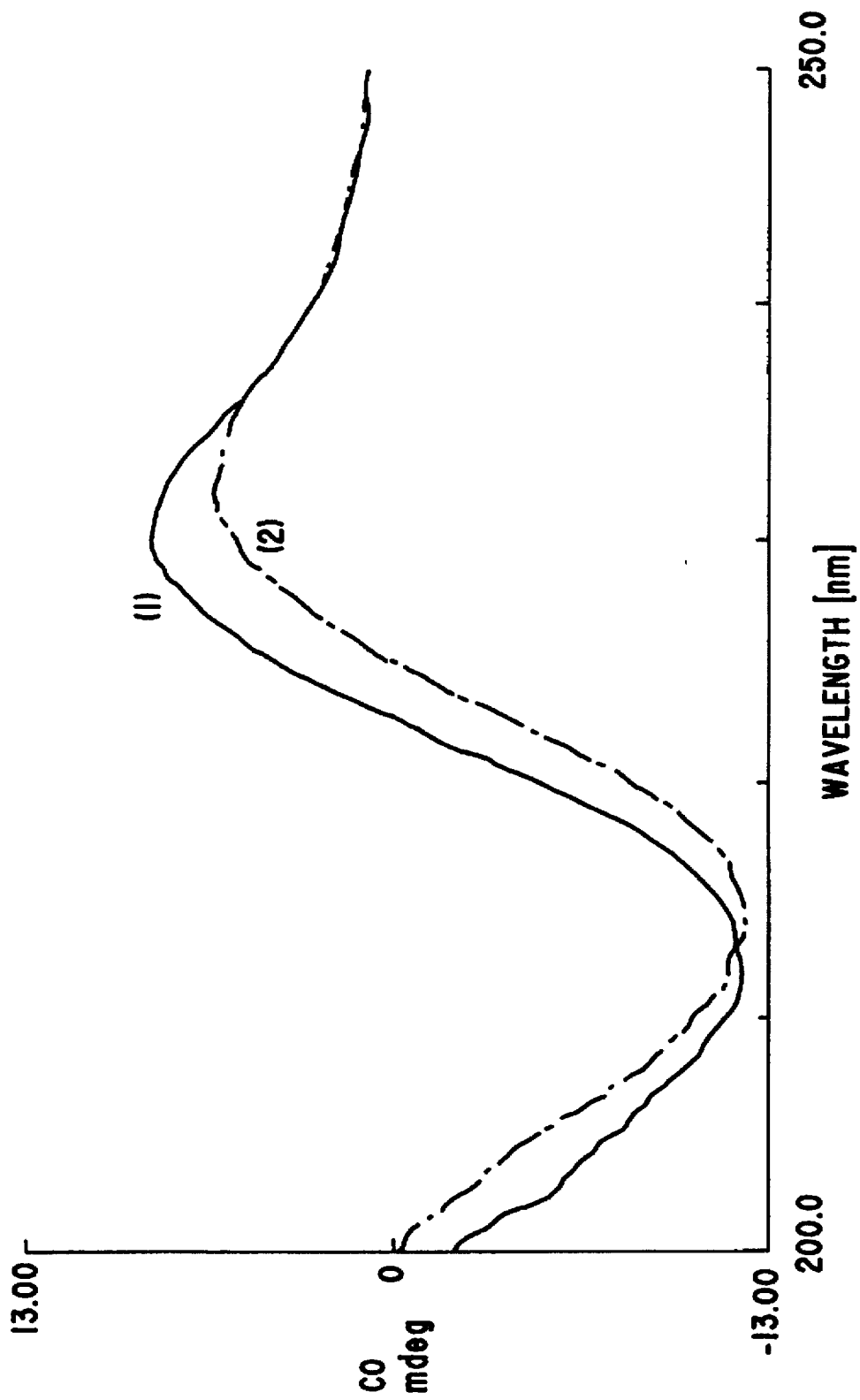

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 387 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
ATGGCCGAAG  CTGGTATCAC  TGGCACCTGG  TATAACCAAC  TGGGGTCGAC  TTTCATTGTG      60
ACCGCTGGTG  CTGACGGAGC  TCTGACTGGC  ACCTACGAAT  CTGCGGTTGG  TAACGCAGAA     120
TCCCGCTACG  TACTGACTGG  CCGTTATGAC  TCTGCACCTG  CCACCGATGG  CTCTGGTACC     180
GCTCTGGGCT  GGACTGTGGC  TTGGAAAAAC  AACTATCGTA  ATGCGCACAG  TGCCACTACG     240
TGGTCTGGCC  AATACGTTGG  CGGTGCTGAG  GCTCGTATCA  ACACTCAGTG  GCTGTTAACA     300
TCCGGCACTA  CCGAAGCGAA  TGCATGGAAA  TCGACACTAG  TAGGTCATGA  CACCTTTACC     360
AAAGTTAAGC  CTTCTGCTGC  TAGCTAA                                           387
```

( 2 ) INFORMATION FOR SEQ ID NO:2:

( i ) SEQUENCE CHARACTERISTICS:
- ( A ) LENGTH: 128 amino acids
- ( B ) TYPE: amino acid
- ( D ) TOPOLOGY: linear ( i i ) MOLECULE TYPE: protein ( x i ) SEQUENCE DESCRIPTION: SEQ ID NO:2:

```
Met Ala Glu Ala Gly Ile Thr Gly Thr Trp Tyr Asn Gln Leu Gly Ser
 1               5                  10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
 65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
            115                 120                 125
```

( 2 ) INFORMATION FOR SEQ ID NO:3:

( i ) SEQUENCE CHARACTERISTICS:
- ( A ) LENGTH: 20 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:3:

```
Ile Asp Ala Ala Lys Lys Ala Gly Val Asn Asn Gly Asn Pro Leu Asp
 1               5                  10                  15

Ala Val Gln Gln
            20
```

( 2 ) INFORMATION FOR SEQ ID NO:4:

( i ) SEQUENCE CHARACTERISTICS:
- ( A ) LENGTH: 12 amino acids
- ( B ) TYPE: amino acid
- ( D ) TOPOLOGY: linear ( i i ) MOLECULE TYPE: peptide ( x i ) SEQUENCE DESCRIPTION: SEQ ID NO:4:

```
Asp Pro Ser Lys Asp Ser Lys Ala Gln Val Ser Ala
 1               5                  10
```

( 2 ) INFORMATION FOR SEQ ID NO:5:

( i ) SEQUENCE CHARACTERISTICS:
- ( A ) LENGTH: 18 base pairs
- ( B ) TYPE: nucleic acid
- ( C ) STRANDEDNESS: single
- ( D ) TOPOLOGY: linear ( i i ) MOLECULE TYPE: DNA ( x i ) SEQUENCE DESCRIPTION: SEQ ID NO:5:

```
CTAGTTAATG ACAGCTGA                                            18
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
AATTACTGTC GACTTCGA                                    18
```

RECOMBINANT CORE STREPTAVIDIN

This is a division of application Ser. No. 08/211,833 filed Apr. 28, 1994 now U.S. Pat. No. 5,489,528.

Streptavidin in its natural form is a tetrameric protein, each subunit being 159 amino acids in length and having a molecular weight of 16,450 Da. Streptavidin is obtained from the culture filtrate of *Streptomyces avidinii* (Chaiet, L. et al., Antimicrob. Agents Chemother. 3 (1963), 28–32). A characteristic of streptavidin, as also of the homologous protein avidin isolated from chicken egg-white, is an exceptionally strong non-covalent binding to the water-soluble vitamin H (d-biotin). One molecule of biotin binds per streptavidin subunit, i.e. four molecules of biotin bind to the tetramet. The dissociation constant of this binding is $10^{-15}$ mol/l. In contrast to avidin, the streptavidin derived from *Streptomyces avidinii* is not glycosylated, does not contain any amino acids containing sulphur and has a lower isoelectric point at ca. pH 6.5. The avidin-biotin system and in particular the streptavidin-biotin system is already widely used in diagnostics and molecular biology (Wilchek, M. and Bayer, E. A., Methods Enzymol. 184 (1990), 5–13 and 14–45). An example of the use of the biotin-streptavidin system is to attach biotin or streptavidin to target molecules, e.g. analytes or to a surface such as e.g. a reagent vessel surface, chromatographic media or biopolymers thus enabling the target molecule to be immobilized or detected.

Streptavidin is usually isolated as a secreted protein from the culture filtrate of *Streptomyces avidinii*. However, these streptavidin preparations are heterogeneous with regard to the N-terminal and/or C-terminal amino acid sequence which is due to proteolysis during the fermentation (long fermentation periods) or/and the purification (Argarana, C. E. et al., Nucl. Acids Res. 14 (1986) 1871–1882; Bayer, E. A. et al., Methods Enzymol. 184 (1990), 80–89; Pähler, A. et al., J. Biol. Chem. 262 (1987) 13933–13937; Hendrickson, W. A. et al., Proc. Natl. Acad. Sci. 86 (1989) 2190–2194; Bayer, E. A. et al., Biochem. J. 259 (1989) 369–376). In addition the complete native streptavidin tends to aggregate (Pähler, A. et al., J. Biol. Chem. 262 (1987) 13933–13937; Bayer, E. A. et al., Biochem. J. 259 (1989) 369–376; Bayer, E. A. et al., J. Biochem. Biophys. Methods 13 (1986) 103–112). As a consequence it is difficult to reproducibly isolate native or biologically active, proteolytically-shortened streptavidin proteins from *S. avidinii*.

The aggregation of native streptavidin to form oligomers which already occurs during the isolation and its low solubility (Pähler, A. et al., J. Biol. Chem. 262 (1987), 13933–13937) also leads to problems when streptavidin is used in a streptavidin-biotin system since a not exactly determinable portion of the streptavidin is withheld from the reaction mixture so that falsifications of the measured results are possible.

A further disadvantage of native streptavidin is that during fermentation and preparation it is proteolytically processed to a limited extent at its N and C terminus. Thus one usually obtains a mixture of different degradation products and the final product of this proteolytic processing is a "core" protein with about 125 to 127 amino acids (Pähler, A. et al., J. Biol. Chem. 262 (1987) 13933–13937; Bayer, E. A. et al., Biochem. J. 259 (1989) 369–376). The proteolytic processing improves the binding properties of streptavidin to biotin conjugates (Bayer, E. A. et al., Biochem. J. 259 (1989) 369–376). However, the mixture of degradation products that is usually obtained does not have exactly reproducible binding properties so that falsifications of the measured results are possible.

The recombinant production of streptavidin is described in EP-B 0 198 015. The heterologous expression and secretion of native streptavidin in *E. coli* by means of the native streptavidin signal sequence resulted in streptavidin variants which are secreted into the periplasma. However, these streptavidin variants denoted ECO avidins are also heterogeneous at their C terminus. Moreover the *S. avidinii* signal sequence is not completely cleaved in *E. coli* and as a result the N terminus of the molecule contains 13 additional amino acids in comparison to native streptavidin.

The heterologous expression of a recombinant streptavidin in *E. coli*, its isolation in the form of inclusion bodies and renaturation are described in a publication by Sano, T. and Cantor, C. R. (Proc. Natl. Acad. Sci. USA 87 (1990), 142–146). This is a N-terminally truncated streptavidin fusion protein which contains the amino acids 15 to 159 of the natural streptavidin molecule. However, it has been shown that part (30 to 50%) of the renatured, purified streptavidin fusion protein aggregates to form oligomers.

The object of the present invention was to provide a homogeneous streptavidin mutant protein (core streptavidin) in which the disadvantages of the prior art are at least partially eliminated. A further object of the present invention was the development of a reliable, simple, reproducible and economic production process for a homogeneous core streptavidin which is suitable for the various analytical and preparative applications and in particular for diagnostic tests.

The object according to the invention is achieved by a process for the isolation of recombinant core streptavidin in which host cells are transformed with a DNA coding for a core streptavidin, the transformed host cells are cultured under suitable conditions, the DNA coding for the core streptavidin is expressed and the recombinant core streptavidin is isolated from the host cells or from the culture medium, which is characterized in that a DNA coding for core streptavidin is used which has (a) the nucleotide sequence shown in SEQ ID NO. 1 or (b) a nucleotide sequence corresponding to the nucleotide sequence (a) within the scope of the degeneracy of the genetic code.

The process according to the invention enables a core streptavidin to be obtained which is homogeneous and is therefore particularly suitable for diagnostic applications. The core streptavidin according to the invention can if desired contain a methionine residue at the N terminus.

The production of the DNA coding for core streptavidin, the transformation of suitable host cells and their culture as well as the expression and isolation of the recombinant product can be carried out according to methods familiar to a person skilled in the art which are typically described in "Molecular Cloning", T. Maniatis, I. F. Fritsch and J. Sambrook, Cold Spring Harbor Laboratory. The production of the DNA coding for core streptavidin can be carried out starting with the streptavidin structural gene (obtainable for example from British Biotechnology Limited) by shortening the 3' end by a DNA fragment which codes for the C-terminal amino acid sequence IleAspAlaAlaLysLysAlaGlyValAsnAsnGlyAsnProLeuAspAlaValGlnGln (SEQ ID NO: 3)

and by shortening the 5' end by a DNA fragment which codes for the N-terminal amino acid sequence AspProSerLysAspSerLysAlaGluValSerAla (SEQ ID NO: 4)

In order to directly express (initiate the translation) of core streptavidin, the sequence ATG coding for Met also has to be attached to the 5' end of the core streptavidin gene. The methionine start codon is in some cases cleaved off again by cellular methionyl-amino-peptidase (Dalboge, H. et al., FEBS L. 266 (1990) 1–3) after translation depending on the host organism used. In contrast to the processing of native streptavidin during secretion and purification from culture filtrates of *S. avidinii*, this processing is limited to the N-terminal methionine residue and the extent of which is determined by the choice of conditions during the culture of the microorganism and during expression so that a product of constant composition which can be produced reproducibly in accordance with the object of the invention is obtained.

The choice of the expression vector depends on the selected host cell. Suitable vectors for the various host cells are familiar to a person skilled in the art and do not need to be elucidated here in more detail.

It is expedient to use a microorganism as the host cell such as a prokaryote or yeast. It is particularly preferably to use *E. coli* in combination with a suitable expression plasmid for *E. coli*. The host cell is transformed in a well-known manner with a recombinant plasmid which contains one or several copies of the DNA coding for the core streptavidin which is used according to the invention. A recombinant expression plasmid is preferably used for this which has a multicopy origin of replication i.e. at least 20 copies and preferably at least 100 copies per cell are present in a transformed cell. The origin of replication of the plasmid pUC19 is for example suitable as a multicopy origin of replication.

In order to produce the core streptavidin according to the invention, the DNA coding for core streptavidin is placed under the control of a promoter which can be readily regulated in the transformed host cell. In this case it is preferable that an additional plasmid is present in the transformed host cell which effects an overexpression of a repressor protein which inactivates the regulatable promoter during the growth phase of the cells. In this embodiment of the inventive process the DNA coding for the core streptavidin can then be expressed by addition of an inductor which activates the regulatable promoter.

The expression conditions are adjusted in a known manner preferably so that the recombinant core streptavidin is produced in the form of so-called inclusion bodies since these can be easily separated from soluble cell components. The inclusion bodies obtained in this way can then be solubilized in a manner which is also known and renatured to form soluble, biologically-active core streptavidin for example according to the process described in EP-A 253 823.

The renatured core streptavidin is then preferably subjected to a fine purification preferably by chromatography. Affinity chromatographic materials, ion exchangers or materials for hydrophobic chromatography are for example suitable for the chromatography.

The invention also concerns a recombinant DNA which codes for a core streptavidin and has (a) the nucleotide sequence shown in SEQ ID NO. 1 or (b) a nucleotide sequence corresponding to the nucleotide sequence (a) within the scope of the degeneracy of the genetic code.

The invention in addition concerns a recombinant vector which contains at least one copy of the recombinant DNA defined above. It is expedient if the base vector is a plasmid, but viral vectors can also be used. The vector of the invention preferably has a multicopy origin of replication. In addition the DNA coding for core streptavidin in the vector according to the invention is preferably under the control of a regulatable promoter.

The invention in addition concerns a host cell which is transformed with the recombinant DNA defined above or with a vector containing the latter.

Finally the invention also concerns recombinant core streptavidin which is characterized by the amino acid sequence shown in SEQ ID NO. 2 with or without an N-terminal methionine residue.

The plasmids and microorganisms mentioned in the present invention were deposited at the "Deutsche Sanumlung yon Mikroorgansimen und Zellkulturen GmbH" (DSM), Mascheroder Weg 1B, D-3300 Braunschweig, according to the rules of the Budapest Treaty and have the following depository numbers:

*E. coli* K12 RM 82 DSM 5445 on 02.10.1991
pSAM-core/pUBS 500 DSM 6720 on 20.09.1991
In the list of sequences
SEQ ID NO. 1 shows the DNA sequence of core streptavidin,
SEQ ID NO. 2 shows the protein sequence of core streptavidin with a N-terminal methionine residue.

BRIEF DESCRIPTION OF THE DRAWINGS

FIGS. 2A and 2B show circular dichroism (CD) spectra of core streptavidin according to the invention (2a) and of conventional core streptavidin of *S. avidinii* (2b) in each case without (curve 1) and with biotin (curve 2).

The following examples serve to elucidate the invention in more detail.

EXAMPLE 1

1.1 Construction of the C-terminally truncated streptavidin gene (plasmid pUC18-BBG9-C)

In the following plasmid construction the 3' end of the native streptavidin structural gene was shortened by a DNA fragment which codes for the C-terminal amino acid sequence IleAspAlaAlaLysLysAlaGlyValAsnAsnGlyAsnProLeu-AspAlaValGlnGln (SEQ ID NO: 3)

For this the plasmid pUC18-BBG9 (pUC18 vector with an inserted streptavidin gene, British Biotechnology Limited (WO89/03422)) was digested with the restriction endonucleases NheI and HindIII, the ca. 2.7 kbp long NheI/HindIIi fragment was isolated and ligated with the synthetic DNA fragment
NheI PvuII
5'-CTAGTTAATGACAGCTGA-3' (SEQ ID NO: 5)
3'-AATTACTGTCGACTTCGA-5' (SEQ ID NO: 6)
AlaSer*** HindIII
***: stop codon
(construction: pUC18-BBG9-C). The desired DNA sequence was confirmed by DNA sequencing.

1.2 Construction of the *E. coli* expression vector pD-NX

The plasmid pD-NX is a derivative of the plasmid pQE-6 (pDS56/RBSII,Ncol) from the Diagen Company (D üsseldorf) from which the chloramphenicol-acetyltransferase gene (CAT) without promoter was removed.

For this the plasmid pDS56/RBSII,Ncol was digested with the restriction endonucleases NheI and XbaI, the ca. 2.6 kbp long Nhei/XbaI vector fragment was isolated and the compatible ends of the NheI and XbaI cleavage sites were linked by ligation (construction: pD-NX).

1.3 Construction of the N-terminally and C-terminally truncated streptavidin gene (plasmid: pSA-core)

In the following plasmid construction the 5' end of the native streptavidin structural gene was shortened by a DNA fragment which codes for the N-terminal amino acid sequence AspProSerLysAspSerLysAlaGlnValSerAla (SEQ ID NO: 4).

For this the plasmid pUC18-BBGg-C which was constructed as described above, was digested with the restriction endonuclease PstI, the 3' overhanging end of the PstI cleavage site was removed by digestion with T4-DNA polymerase, the DNA was recleaved with HindIII, the ca. 390 bp long Psti(blunt)/HindIII streptavidin fragment was isolated and ligated into the ca. 2.6 kbp long NcoI(blunt)/HindIII pD-NX vector fragment after filling in the 5' overhanging end of the NcoI cleavage site with Klenow polymerase (construction: pSA-core).

1.4 Construction of the core streptavidin multicopy expression plasmid pSAM-core In order to increase the plasmid copy number (gene dose effect) in $E.$ $coli$, the pMB1 origin of replication of the plasmid pSA-core was replaced by the origin of replication of the multicopy plasmid pUC19 (Chambers, S. P. et al., Appl. Microbiol. Biotechnol. 29 (1988) 572-578).

Figure 1:
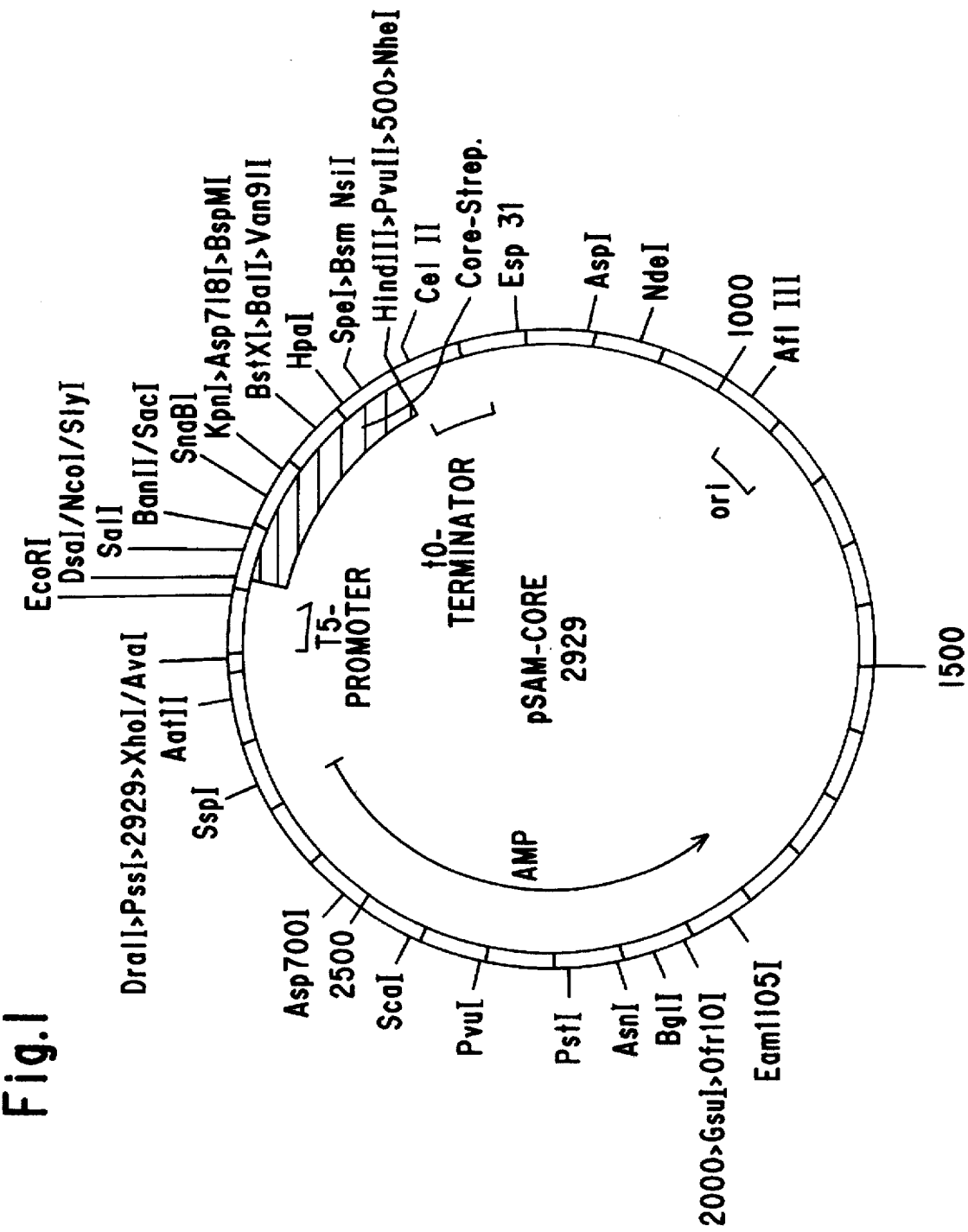
FIG. 1 shows the plasmid map of the core streptavidin expression plasmid pSAM core.

For this the ca. 1 kbp long AflIII/BglII fragment from pSA-core was replaced by the analogous fragment from pUC19 (Yanish-Perron, C. et al., Gene 33 (1985) 103-119) (construction: pSAM-core). The plasmid map of pSAM-core is shown in FIG. 1. The plasmid pSAM-core is deposited as a plasmid mixture with pUBS500 under DSM 6720.

EXAMPLE 2

Expression of core streptavidin in $E.$ $coli$

For the expression of core streptavidin, the $E.$ $coli$ K12 strain RM82 (DSM 5445) (a methionine revertant of ED 8654, Murray, N. E. et al., Mol. Gen. Genet. 150 (1977) 53-61) was transformed with the core streptavidin expression plasmid pSAM-core (ampicillin resistance) and the lacI$^q$ repressor plasmid pUBS500 (kanamycin resistance, construction and description see: EP-A 0 373 365).

The RM82/pUBS500/pSAM-core cells were cultured in DYT medium (1% (w/v) yeast extract, 1% (w/v) Bacto tryptone, Difco, and 0.5% NaCl) containing 50 mg/l ampicillin and 50 mg/l kanamycin up to an optical density at 550 nm of 0.6-0.9 and subsequently induced with IPTG (final concentration 1-5 mmol/l). After an induction phase of 4-8 hours, the cells were harvested by centrifugation, washed with 25 mmol/l Tris-HCl buffer, pH 7.5 and stored at -20° C. until further processing.

EXAMPLE 3

Core streptavidin expression analysis in $E.$ $coli$

The cell pellet from 1 ml centrifuged culture medium (RM82/pUBS500/pSAM-core cells) was resuspended in 0.25 ml 10 mmol/l phosphate buffer, pH 6.8 and 1 mmol/l EDTA and the cells were lysed by ultrasonic treatment. After centrifugation, ⅕ volumes 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction was resuspended in 0.3 ml 1×SDS sample buffer with 6-8M urea, the samples were incubated for 5 minutes at 95° C. and centrifuged. Afterwards the proteins were separated by SDS polyacrylamide gel electrophoresis (PAGE) (Laemmli, U. K., Nature 227 (1970) 680-685) and stained with Coomassie brilliant blue R dye.

The electrophoretically separated proteins were also transferred onto nitrocellulose filters, immobilized (Towbin, H. et al., Proc. Natl. Acad. Sci. 76 (1979) 4350) and the streptavidin-immunoreactive proteins were detected with a specific anti-streptavidin antiserum from sheep.

The core streptavidin protein synthesized in $E.$ $coli$ was homogeneous and was found exclusively in the insoluble cell debris fraction (IB's). No truncated core streptavidin fragments were detectable by SDS PAGE and Western blot analysis. The expression yield for core streptavidin was 30-50% in relation to the total $E.$ $coli$ protein. The protein sequence of the core streptavidin is shown in SEQ ID NO.2.

EXAMPLE 4

Preparation of active core streptavidin from $E.$ $coli$ 4.1 Cell lysis and preparation of inclusion bodies (IB's)

40 g (wet weight) $E.$ $coli$ RM82/pUBS500/pSAM-core cells were suspended in 200 ml 0.1 mol/l Tris-HCl, pH 7.0 at 0° C.. 60 mg lysozyme was added and they were incubated for 20 minutes at 0° C. After addition of 2 mmol/l $MgCl_2$ and 1 mg/100 ml DNase (Boehringer Mannheim GmbH, Cat. No. 104159), the cells were completely mechanically disrupted by means of high pressure dispersion and the DNA was subsequently digested for 30 minutes at 25° C. The lysis solution was subsequently admixed with 100 ml 60 mmol/l EDTA, 6% Triton X100 and 1.5 mol/l NaCl, pH 7.0 and incubated for a further 30 minutes at 0° C. Afterwards the insoluble components (cell debris and IB's) were sedimented by centrifugation using a Sorvall centrifuge.

The pellet was resuspended in 200 ml 0.1 mol/l Tris-HCl, 20 mmol/l EDTA, pH 6.5 and incubated for 30 minutes at 25° C. The IB preparation was then isolated by centrifugation.

4.2 Solubilisation of the IB's 10 g IB pellet (wet weight) was suspended in 40 ml 0.1 mol/l Tris-HCl, 6 mol/l guanidine-HCl, 10 mmol/l EDTA, pH 7.0 by stirring for 1.5 hours at 4° C. The insoluble components were separated by centrifugation and the clear supernatant was dialysed against 0.1 mol/l Tris-HCl, 6 mol/l guanidine-HCl, 10 mmol/l EDTA, pH 7.0 (3×3 1, 24 hours, 4° C.).

4.3 Renaturation

The renaturation was carried out at 25° C. by a 20-fold addition of 2 ml aliquots of core streptavidin solubilisate (40 mg/ml) into 1.6 l 0.1 mol/l sodium phosphate, 5 mmol/l EDTA, pH 7.0 at intervals of 20 minutes.

After completion of the renaturation reaction, insoluble components were separated by centrifugation and the clear supernatant containing core streptavidin was processed further.

4.4 Concentration and/or dialysis of the renaturation preparation

The renaturation preparation can be concentrated as required by membrane filtration and/or dialysed against a desired buffer to remove guanidine-HCl.

EXAMPLE 5

Purification of renatured core streptavidin from $E.$ $coli$

Core streptavidin from renaturation preparations can if required be purified further using chromatographic methods which are well-known to a person skilled in the art.

Purification of core streptavidin by ion exchange chromatography on Q-Sepharose-ff after prior concentration and dialysis The renaturation preparation was concentrated to 120 ml by ultrafiltration in a stirred cell, it was centrifuged to remove insoluble residues and subsequently dialysed against 20 mmol/l Tris-HCl, pH 8.5, (2×10 l, 24 hours, 4° C.). A Q-Sepharose-ff column (3×28 cm, V=200 ml) equilibrated with the same buffer was loaded with the concentrated and dialysed renaturation preparation (1 column volume/hour, 1 CV/h) and washed with equilibration buffer until the absorbance of the eluate at 280 nm had reached the blank value of the buffer. The bound material was eluted with a gradient of 0 to 150 mmol/l NaCl in equilibration buffer (10 CV, 1 CV/h).

|  | Volume ml | Activity[1] Units/ml | $C^{Prot}$ mg/ml | $SA^{2}$ units/ml |
|---|---|---|---|---|
| Dialysate | 180 | 34.8 | 2 | 17.4 |
| Q-eluate | 200 | 24.8 | 1.3 | 19.4 |

[1] Activity in the titration test (cf. example 6.2)
[2] Specific activity: Activity in the titration test divided by the protein content of the sample.

Suitable fractions from the elution were pooled (V=200 ml), concentrated in a stirred cell, dialysed against redistilled water (2×15 l, 70 hours, 4° C.), frozen and lyophilized.

EXAMPLE 6

Characterization of purified core streptavidin from *E. coli*

6.1 SDS PAGE

The homogeneity and purity of renatured, purified core streptavidin was examined by SDS PAGE (Laemmli, U. K., Nature 227 (1970) 680–685).

Renatured, purified core streptavidin was homogeneous (single band) in the SDS PAGE (molecular weight: ca. 13,500 Da) and had a purity of >98% with ca. 70–90% processing of the N-terminal methionine.

6.2 Determination of the activity (biotin binding test)

The activity of core streptavidin was determined by titration with biotin while monitoring the change in absorbance at 233 nm caused by the complex formation. 1 unit is defined as the binding of 1 µg biotin by the sample.

The protein determination was carried out by measuring the absorbance at 280 nm. The extinction coefficient of a 1% solution is $\epsilon=34$ at 280 nm (Green, M., Methods Enzymol. 184 (1990) 51–67).

The measured specific activity (19.4 units/mg protein) corresponds to a binding stoichiometry biotin:core streptavidin$\geq 1$ (relative to the monomer).

6.3 Spectroscopic characterization

The structural change caused by biotin binding was monitored by means of CD spectroscopy. For this spectra were recorded before and after addition of biotin and these were compared with spectra obtained in the same way of core streptavidin produced conventionally from *S. avidinii*.

The spectra were recorded under the following conditions in a Jasco J-600 CD spectrometer: rec core streptavidin or core streptavidin from *S. avidinii* (lyophilisate) was dissolved at a concentration of 2 µmol/l in redistilled water, placed in a cuvette with a light path of 5 mm and measured with a scan rate of 20 nm/minute in the range 200 to 250 nm against redistilled water in the reference cuvette at a damping (time const.) of 8 seconds. Subsequently biotin was added to the measuring cuvette at a concentration of ca. 6 µmol/l and afterwards the spectrum was recorded again under the same conditions.

Figure 2A:
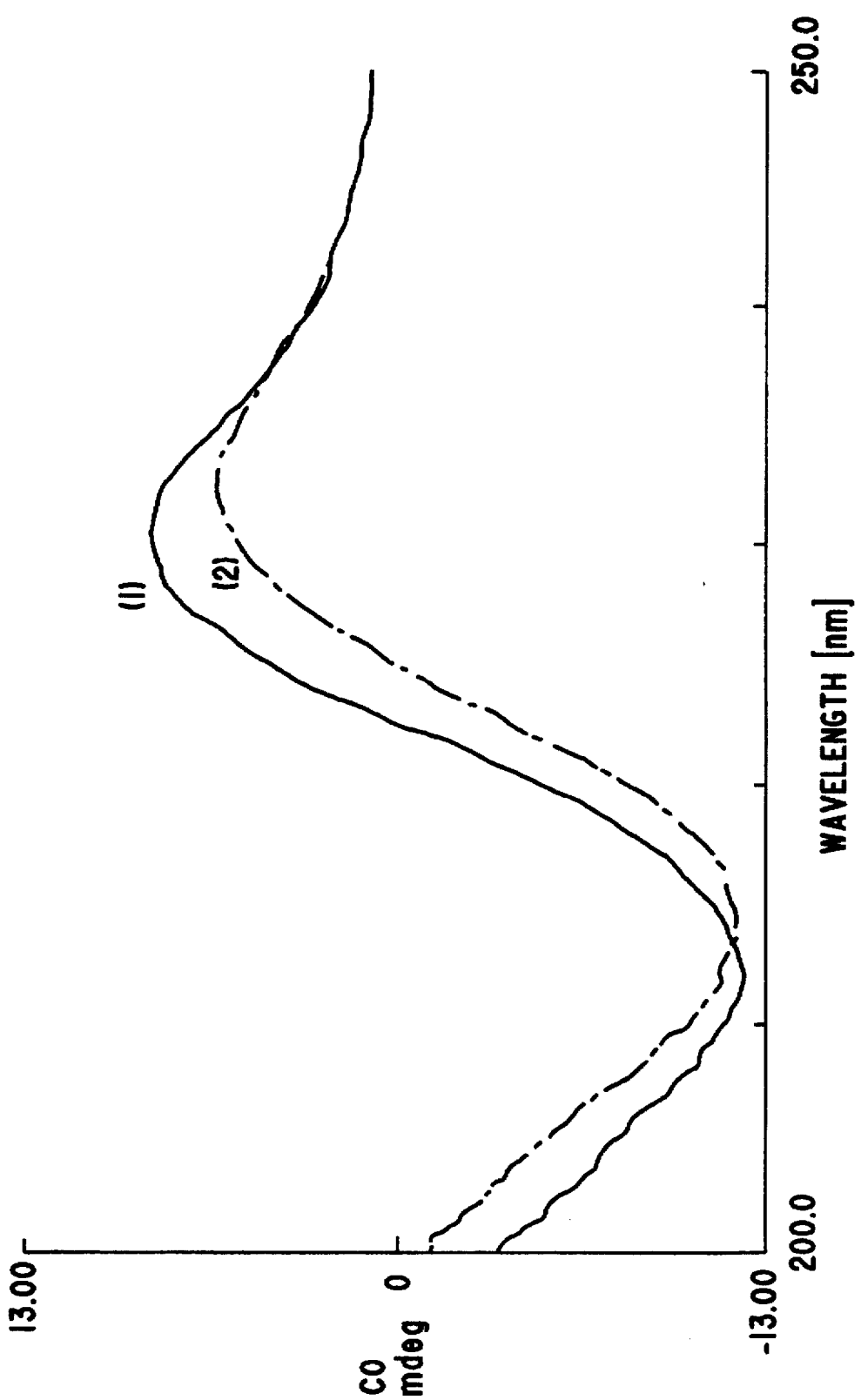

Spectra of purified core streptavidin from *E. coli* (FIG. 2a) and spectra of conventionally prepared core streptavidin from *S. avidinii* (FIG. 2b) do not differ.

---

We claim:

1. A recombinant core streptavidin consisting of the amino acid sequence shown in SEQ ID NO: 2.

2. A method for immobilizing or detecting a target molecule in a diagnostic procedure or an affinity chromatography procedure comprising attaching a recombinant core streptavidin consisting of the amino acid sequence shown in SEQ ID NO: 2 to said target molecule and immobilizing or detecting said target molecule.

\* \* \* \* \*